US008969024B2

(12) United States Patent
Kaymakcalan et al.

(10) Patent No.: US 8,969,024 B2
(45) Date of Patent: Mar. 3, 2015

(54) COMPOSITIONS AND METHODS COMPRISING BINDING PROTEINS FOR ADALIMUMAB

(75) Inventors: Zehra Kaymakcalan, Westborough, MA (US); Limin Xiong, Shrewsbury, MA (US)

(73) Assignee: AbbVie Biotechnology Ltd, Hamilton (BM)

( * ) Notice: Subject to any disclaimer, the term of this patent is extended or adjusted under 35 U.S.C. 154(b) by 1352 days.

(21) Appl. No.: 12/229,788

(22) Filed: Aug. 27, 2008

(65) Prior Publication Data

US 2009/0068172 A1 Mar. 12, 2009

Related U.S. Application Data

(60) Provisional application No. 60/966,410, filed on Aug. 28, 2007.

(51) Int. Cl.

| | |
|---|---|
| C07K 16/42 | (2006.01) |
| C12N 5/20 | (2006.01) |
| C12P 21/08 | (2006.01) |
| G01N 33/536 | (2006.01) |
| G01N 33/543 | (2006.01) |
| G01N 33/563 | (2006.01) |
| G01N 33/577 | (2006.01) |
| G01N 33/68 | (2006.01) |
| G01N 33/58 | (2006.01) |
| C12N 5/16 | (2006.01) |
| G01N 33/60 | (2006.01) |

(52) U.S. Cl.
CPC ........ *C07K 16/4241* (2013.01); *G01N 33/6857* (2013.01); *G01N 33/543* (2013.01); *G01N 33/581* (2013.01); *C12N 5/163* (2013.01); *G01N 33/60* (2013.01); *G01N 33/536* (2013.01); *G01N 33/686* (2013.01); *C07K 2317/55* (2013.01); *C07K 2317/56* (2013.01); *Y10S 435/975* (2013.01); *Y10S 530/866* (2013.01)
USPC ......... 435/7.94; 435/7.1; 435/7.92; 435/7.93; 435/70.21; 435/327; 435/328; 435/337; 435/975; 436/512; 436/518; 436/536; 436/548; 436/164; 530/387.2; 530/387.3; 530/388.25; 530/388.9; 530/391.1; 530/866

(58) Field of Classification Search
CPC ........... C07K 16/4241; C07K 2317/55; C07K 2317/56; C12N 5/163; G01N 33/536; G01N 33/543; G01N 33/581; G01N 33/60; G01N 33/6857; G01N 33/686
USPC ............ 435/7.1, 7.92, 7.93, 7.94, 70.21, 327, 435/328, 337, 975; 436/512, 518, 536, 548, 436/164; 530/387.2, 387.3, 388.25, 388.9, 530/391.1, 866
See application file for complete search history.

(56) References Cited

U.S. PATENT DOCUMENTS

| | | | | |
|---|---|---|---|---|
| 5,665,558 | A | * | 9/1997 | Frame et al. ................. 435/7.25 |
| 6,258,562 | B1 | * | 7/2001 | Salfeld et al. ................ 435/69.6 |
| 6,555,321 | B1 | * | 4/2003 | Daniel et al. .................. 435/7.1 |
| 2006/0099662 | A1 | * | 5/2006 | Chuntharapai et al. ...... 435/7.92 |
| 2006/0286108 | A1 | | 12/2006 | Bell |
| 2007/0172897 | A1 | | 7/2007 | Maksymowych et al. |

FOREIGN PATENT DOCUMENTS

| | | |
|---|---|---|
| EP | 0568500 A1 | 11/1993 |
| EP | 0614984 A2 | 9/1994 |
| EP | 1917854 A1 | 5/2008 |
| GB | 2279077 A | 12/1994 |
| WO | 90/06515 * | 6/1990 |
| WO | WO-92/16553 A1 | 10/1992 |
| WO | WO-93/06213 A1 | 4/1993 |
| WO | WO-95/17200 A1 | 6/1995 |
| WO | WO-97/29131 A1 | 8/1997 |

OTHER PUBLICATIONS

Abbott Laboratories, 2010. HUMIRA (adalimumab) Prescribing Information and Medication Guide. Downloaded Feb. 17, 2011 from www.rxabbott.com/pdf/humira.pdf.*
Bartelds et al., Feb. 4, 2007. Clinical response to adalimumab: relationship to anti-adalimumab antibodies and serum adalimumab concentrations in rheumatoid arthritis. Ann. Rheum. Dis. 66: 921-926.*
Wolbink et al., 2005. Relationship between serum trough infliximab levels, pretreatment C reactive protein levels, and clinical response to infliximab treatment in patients with rheumatoid arthritis. Ann. Rheum. Dis. 64: 704-707.*
Cvetković et al., 2006. Adalimumab. A review of its use in adult patients with rheumatoid arthritis. Biodrugs 20: 293-311.*
McLaughlin et al., 1998. Rituximab chimeric anti-CD20 monoclonal antibody therapy for relapsed indolent lymphomaq: half of patients respond to a four-dose treatment program. (J. Clin. Oncol. 16: 2825-2833.*
Emery P. Adalimumab therapy: clinical findings and implications for integration into clinical guidelines for rheumatoid arthritis. Drugs Today (Barc). Mar. 2005;41(3):155-63.

(Continued)

*Primary Examiner* — Gail R Gabel
*Assistant Examiner* — James L Grun
(74) *Attorney, Agent, or Firm* — McCarter & English, LLP; Cristin H. Cowles; Mei Bai

(57) ABSTRACT

Compositions and methods comprising proteins that bind specifically to adalimumab are disclosed herein. Adalimumab is a monoclonal antibody specific for the cytokine TNF-α and was developed to treat TNF-α mediated inflammatory diseases. In one aspect of the instant invention, the binding proteins are antibodies directed toward adalimumab. These antibodies, including binding fragments thereof, can be used in a clinical setting as well as for research and development. For example, these anti-adalimumab antibodies can be employed to neutralize adalimumab.

14 Claims, No Drawings

(56) References Cited

OTHER PUBLICATIONS

Galloway, C.J., et al. "Anti-tumor necrosis factor receptor and tumor necrosis factor agonist activity by an anti-idiotypic antibody," *Eur. J. Immunol.* 22(11):3045-3048 (1992).

Griffiths, A.D., et al. "Human anti-self antibodies with high specificity from phage display libraries," EMBO J. 12(2):725-34 (1993).

International Search Report dated Jun. 9, 1997 as cited in WO/1997/029131.

Chow et al. Clinical Research, vol. 42, No. 2, Apr. 1994, p. 299a XP002032300, "Effect of monoclonal antibody to human TNF on TNFalpha, IL-1 beta and IL-6 levels in patents with sepsis syndrome".

\* cited by examiner

COMPOSITIONS AND METHODS COMPRISING BINDING PROTEINS FOR ADALIMUMAB

RELATED APPLICATIONS

This application claims priority to and the benefit of U.S. Provisional Application No. 60/966,410, filed Aug. 28, 2007.

FIELD OF THE INVENTION

The present invention is directed toward binding proteins specific for adalimumab. In one aspect, the binding proteins are antibodies. These binding proteins have utility in a clinical setting as well as in research and development.

BACKGROUND OF THE INVENTION

Tumor necrosis factor-α (hereinafter, TNF) is a multifunctional pro-inflammatory cytokine secreted predominantly by monocytes/macrophages that has effects on lipid metabolism, coagulation, insulin resistance, and endothelial function. TNF is a soluble homotrimer of 17 kD protein subunits. A membrane-bound 26 kD precursor form of TNF also exists. It is found in synovial cells and macrophages in tissues. Cells other than monocytes or macrophages also produce TNF. For example, human non-monocytic tumor cell lines produce TNF as well as CD4$^+$ and CD8$^+$ peripheral blood T lymphocytes and some cultured T and B cell lines produce TNF. It is involved in, but not unique to, rheumatoid arthritis, and occurs in many inflammatory diseases. Receptors for TNF are on several mononuclear cells, in the synovial membrane, as well as the peripheral blood and synovial fluid. TNF is a critical inflammatory mediator in rheumatoid arthritis, and may therefore be a useful target for specific immunotherapy.

TNF causes pro-inflammatory actions which result in tissue injury, such as degradation of cartilage and bone, induction of adhesion molecules, inducing pro-coagulant activity on vascular endothelial cells, increasing the adherence of neutrophils and lymphocytes, and stimulating the release of platelet activating factor from macrophages, neutrophils and vascular endothelial cells. Recent evidence associates TNF with infections, immune disorders, neoplastic pathologies, autoimmune pathologies and graft-versus-host pathologies.

TNF is believed to play a central role in gram-negative sepsis and endotoxic shock, including fever, malaise, anorexia, and cachexia. Endotoxin strongly activates monocyte/macrophage production and secretion of TNF and other cytokines. TNF and other monocyte-derived cytokines mediate the metabolic and neurohormonal responses to endotoxin. Endotoxin administration to human volunteers produces acute illness with flu-like symptoms including fever, tachycardia, increased metabolic rate and stress hormone release. Circulating TNF increases in patients suffering from gram-negative sepsis. Neutralizing antisera or monoclonal antibodies to TNF have been shown in mammals to abrogate adverse physiological changes and prevent death after lethal challenge in experimental endotoxemia and bacteremia.

Thus, TNF has been implicated in inflammatory diseases, autoimmune diseases, viral, bacterial and parasitic infections, malignancies, and/or neurodegenerative diseases and is a useful target for specific biological therapy in diseases, such as rheumatoid arthritis and Crohn's disease. Beneficial effects in open-label trials with a chimeric monoclonal antibody to TNF have been reported with suppression of inflammation and with successful re-treatment after relapse in rheumatoid arthritis and in Crohn's disease.

Adalimumab (also known by its trademark HUMIRA® available from Abbott Laboratories) is a recombinant human monoclonal antibody specific for TNF-α. This monoclonal antibody binds to TNF and blocks its interaction with the p55 and p75 cell-surface TNF receptors. See, U.S. Pat. No. 6,090,382, the entire teaching of which is incorporated herein by reference.

As previously stated, TNF plays a significant role in the pathological inflammatory process. Adalimumab is clinically used to treat pathological inflammatory processes such as rheumatoid arthritis. For clinical applications and scientific research there is a need to have binding proteins, such as antibodies, capable of binding specifically to adalimumab. In the clinical setting, subjects receiving adalimumab may experience an adverse response due to, e.g., excessive adalimumab or an unusual sensitivity toward the antibody. In some cases, patients who are under adalimumab treatment might contract a serious infection where biologically active TNF is essential for the control of the infection. Further, in order to investigate adalimumab and its role in the treatment of certain pathologies it is necessary to qualitatively and quantitatively examine adalimumab in a sample matrix. The present provides binding proteins specific for adalimumab which can be used to effectuate these goals.

SUMMARY OF THE INVENTION

The present invention is directed to proteins that bind specifically to adalimumab. Adalimumab is a monoclonal antibody specific for the cytokine TNF-α and was developed to treat TNF-α mediated inflammatory diseases. In one aspect of the instant invention, the binding proteins are antibodies directed toward adalimumab. These antibodies, including antigen-binding fragments thereof, can be used in a clinical setting as well as for research and development.

In one embodiment, the binding proteins of the present invention are anti-adalimumab antibodies, or antigen-binding portions thereof. These anti-adalimumab antibodies can be used, e.g., to neutralize adalimumab by preventing the binding of adalimumab to its target TNF. One aspect of this embodiment pertains to pharmaceutical compositions comprising anti-adalimumab antibodies or antigen-binding fragments thereof. These pharmaceutical compositions can be used to treat a subject in need thereof where the subject is, e.g., experiencing sensitivity toward adalimumab.

The present invention further relates to one or more antibodies that specifically bind to adalimumab including fragments, modifications, and derivatives thereof and can be used in both a clinical and research setting. In a particular aspect, these antibodies are one or more monoclonal antibodies each having different specific binding characteristics. The monoclonal antibodies provided herein have binding affinities sufficient to detect adalimumab including fragments, modifications, and derivatives thereof in a sample matrix. These antibodies can also be used in assays to detect adalimumab bound TNF complexes.

The invention further provides one or more kits comprising anti-adalimumab antibodies including antigen-binding portions thereof that can be used in a pharmaceutical composition to, e.g., neutralize adalimumab. Further, these kits comprise reagents used to detect and quantify adalimumab in a sample.

DETAILED DESCRIPTION OF THE INVENTION

The present invention is directed to proteins that bind specifically to adalimumab. Adalimumab is a monoclonal antibody specific for the cytokine TNF-α and was developed to treat TNF-α mediated inflammatory diseases. In one aspect of the instant invention, the binding proteins are antibodies directed toward adalimumab. These antibodies, including antigen-binding fragments thereof, can be used in a clinical setting as well as for research and development.

This invention pertains to adalimumab binding proteins. In one aspect the binding proteins are anti-adalimumab antibodies, or antigen-binding portions thereof. In a particular aspect, these antibodies include CDR graft antibodies, humanized antibodies, and fragments thereof, all capable of binding to adalimumab. The invention also pertains to pharmaceutical compositions comprising anti-adalimumab antibodies including antigen-binding fragments thereof.

These anti-adalimumab antibodies, and fragments thereof, can be used to, e.g., neutralize adalimumab by preventing the binding of adalimumab to its target TNF. This inhibition can be effectuated in an in vivo or in vitro environment. The antibodies of the present invention can also be employed in detecting adalimumab in a sample, e.g., in a biological sample. These antibodies can also be used in assays to detect adalimumab bound TNF complexes.

In order that the present invention may be more readily understood, certain terms used herein are first defined. Additional definitions are set forth throughout the detailed description.

The terms "tumor necrosis factor," "tumor necrosis factor-α," "TNF-α" and "TNF" are used interchangeably herein, unless the context dictates otherwise, and include any variants which occur in nature or synthetically manufactured. This same notion holds true for the terms "adalimumab" and "HUMIRA."

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains comprise a binding domain that interacts with an antigen. The constant regions of antibodies may mediate the binding of the immunoglobulin to host tissues or factors, including various cells of the immune system through Fc receptors (e.g., effector cells) and the first component (Clq) of the classical complement system.

It is important to note that when reference is made to an anti-adalimumab antibody it is understood that this embraces the notion of antigen-binding portions/fragments thereof, unless the context dictates otherwise. Also, when reference is made to adalimumab it is understood that fragments, derivatives and modifications thereof are also included unless the context dictates otherwise.

The term "antigen-binding portion" of an antibody (or simply "antibody portion"), as used herein, refers to one or more fragments of an antibody that retains the ability to specifically bind to an antigen (e.g., adalimumab). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment comprising the $V_H$ and $C_H1$ domains; (iv) a Fv fragment comprising the $V_L$ and $V_H$ domains of a single arm of an antibody, (v) a dAb fragment (Ward et al., (1989) Nature 341:544 546, the entire teaching of which is incorporated herein by reference), which comprises a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al. (1988) Science 242:423 426; and Huston et al. (1988) Proc. Natl. Acad. Sci. USA 85:5879 5883, the entire teachings of which are incorporated herein by reference). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "monoclonal antibody" as used herein, refers to an antibody which displays a single binding specificity and affinity for a particular epitope. Accordingly, the term "human monoclonal antibody" refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

An "isolated antibody", as used herein, is intended to refer to an antibody which is substantially free of other antibodies having different antigenic specificities (e.g., an isolated antibody that specifically binds to adalimumab is substantially free of antibodies that specifically bind antigens other than adalimumab). An isolated antibody that specifically binds to an epitope of adalimumab may, however, have cross-reactivity to other human antibodies. However, the antibody desirably binds to adalimumab. In addition, an isolated antibody is typically substantially free of other cellular material and/or chemicals. In one embodiment of the invention, a combination of "isolated" monoclonal antibodies having different adalimumab specificities are combined in a well defined composition.

As used herein, "specific binding" refers to antibody binding to an epitope present on an antigen but not to other epitopes or antigens. Typically, the antibodies of the present invention bind with an affinity ($K_D$) ranging from approximately $10^{-6}$ M to $10^{-12}$ M or even lower. In one aspect, the $K_D$ ranges from about $10^{-8}$ M to about $10^{-9}$ M. The phrases "an antibody recognizing an antigen" and "an antibody specific for an antigen" are used interchangeably herein with the term "an antibody which binds specifically to an antigen".

The term "$K_D$", as used herein, is intended to refer to the dissociation equilibrium constant of a particular antibody-antigen interaction.

As used herein, "isotype" refers to the antibody class (e.g., IgM or IgG1) that is encoded by heavy chain constant region genes.

As used herein, the term "subject" includes any human or non-human animal. For example, the methods and compositions of the present invention can be used to treat a subject with an inflammatory disease, such as arthritis, e.g., rheumatoid arthritis. The term "non-human animal" includes all vertebrates, e.g., mammals and non-mammals, such as non-human primates, sheep, dog, cow, chickens, amphibians, reptiles, etc.

Anti-adalimumab antibodies of the present invention can be generated by hybridoma technology and then produced by a cell line, a mixed cell line, an immortalized cell or clonal population of immortalized cells, well known in the art. See, e.g., Kohler and Milstein, Nature, 256:495 97 (1975); De St. Groth and Scheidegger, J. Immunol. Meth., 35: 1 21 (1980); E. Harlow and D. Lane, ed., "Antibodies: A Laboratory Manual", (1988), Cold Spring Harbor Laboratory, Cold Spring Harbor, N.Y.; Hammerback and Vallee, J. Biol. Chem., 265: 12763 (1990), Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

Antibodies that are specific for adalimumab or fragments thereof can be raised against an appropriate immunogenic antigen, such as isolated and/or adalimumab or a portion thereof (including synthetic molecules, such as synthetic peptides). Other specific or general antibodies can be similarly raised. Preparation of immunogenic antigens, and monoclonal antibody production can be performed using any suitable technique known in the art.

In one approach, a hybridoma can be produced by fusing a suitable immortal cell line, e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel and Colligan, Immunology, chapter 2, entirely incorporated herein by reference.

Antibody producing cells can also be obtained from the peripheral blood or the spleen or lymph nodes, of humans or other suitable animals that have been immunized with an antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library, e.g., but not limited to, a bacteriophage, ribosome, oligonucleotide, RNA, cDNA, or the like, display library; e.g., as available from Cambridge Antibody Technologies, Cambridgeshire, UK; MorphoSys, Martinsreid/Planegg, Del.; Biovation, Aberdeen, Scotland, UK; BioInvent, Lund, Sweden; Dyax Corp., Enzono, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350, 260 (May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); EP 614 989 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988), the entire teachings of which are incorporated herein by reference).

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www.ncbi.nlm.nih.gov/entrez/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH05/kuby05.htm; www.library.thinkquest.org/12429/Immune/Antibody.html; www.hhmi.org/grants/lectures/1996/vlab/; www.path.cam.ac.uk/.about.mrc7/mikeimages.html; www.antibodyresource.com/; mcb.harvard.edu/BioLinks/Immunology.html.www.immunologylink.com/; pathbox.wustl.edu/.about.hcenter/index.html; www.biotech.ufl.edu/.about.hcl/; www.pebio.com/pa/340913/340913.html; www.nal.usda.gov/awic/pubs/antibody/; www.m.ehime-u.acjp/.about.yasuhito/Elisa.html; www.biodesign.com/table.asp; www.icnet.uk/axp/facs/davies/links.html; www.biotech.ufl.edu/.about.fccl/protocol.htrnl; www.isac-net.org/sites_geo.html; aximt1.imt.uni-marburg.de/.about.rek/AEPStart.html; baserv.uci.kun.nl/.about jraats/links1.html; www.recab.uni-hd.de/immuno.bme.nwu.edu/; www.mrc-cpe.cam.ac.uk/imt-doc/public/INTRO.html; www.ibt.unam.mx/vir/V_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOseminar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stat_aim.html; www.biosci.missouri.edu/smithgp/index.html; www.cryst.bioc.cam.ac.uk/.about.fmolina/Web-pages/Pept/spottech.html; www.jerini.de/fr_products.htm; www.patents.ibm.com/ibm.html. Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976, 862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630; US91/05939, US94/01234, GB89/01334, GB91/01134, GB92/01755; WO90/14443, WO90/14424, WO90/14430, EP 229246, each entirely incorporated herein by reference, included references cited therein.

The anti-adalimumab antibody of the present invention can also be optionally generated by immunization of a transgenic animal (e.g., mouse, rat, hamster, non-human primate, and the like) capable of producing a repertoire of human antibodies, as described herein and/or as known in the art. Cells that produce a human anti-adalimumab antibody can be isolated from such animals and immortalized using suitable methods, such as the methods described herein.

Transgenic mice that can produce a repertoire of human antibodies that bind to human antigens can be produced by known methods, including, but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapati et al. EP 0710 719 A1, Kucherlapati et al. U.S. Pat. No. 6,075,181, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference. Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Anti-adalimumab antibodies as well as the targets (i.e., adalimumab) of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-adalimumab antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by Scatchard Plot Analysis. Competition with a second antibody can also be determined using radioimmunoassay (RIA). In this case, the antigen is incubated with antibody of interest conjugated to a labeled compound (e.g., $^{3}H$ or $^{125}I$) in the presence of increasing amounts of an unlabeled second antibody. However, another method to determine the affinity of an antibody for an antigen is to use the surface Plasmon technology, namely the BIA core instrument. In this method the antibody is captured on a biosensor chip with covalently coupled secondary antibodies, e.g., goat anti-mouse immunoglobulin antibody. Various concentrations of antigen are then flowed through the biosensor chip and the amount of bound material is recorded as a function of time creating what is called a sensorgram. Similarly, dissociation of the antigen recorded by flowing a buffer only can be accomplished. The sensorgrams are analyzed by a special software program used to calculate the on- and off-rates and Kd of the reaction.

An anti-adalimumab antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, e.g., yeast, higher plant, insect and mammalian cells. Depending upon the host employed in a recombinant production procedure, the antibody of the present invention can be glycosylated or can be non-glycosylated. Such methods are described in many standard laboratory manuals, such as Sambrook, Sections 17.37-17.42; Ausubel, Chapters 10, 12, 13, 16, 18 and 20, Colligan, Protein Science, Chapters 12-14, all entirely incorporated herein by reference.

In another aspect, the present invention provides a composition, e.g., a pharmaceutical composition, comprising one or a combination of anti-adalimumab antibodies, or antigen-binding portion(s) thereof, of the present invention, formulated together with a pharmaceutically acceptable carrier. In one aspect, the compositions include a combination of multiple (e.g., two or more) isolated anti-adalimumab antibodies or antigen-binding portions thereof. In a particular aspect, each of the antibodies of the composition binds to a distinct epitope of adalimumab.

The present invention is further directed to antibody-based therapies which involve administering anti-adalimumab antibodies of the invention to a subject, including but not limited to a human, for treating one or more conditions. One condition can be associated with an adalimumab-associated sensitivity, toxicity or pathology. Therapeutic compounds of the invention include, but are not limited to, anti-adalimumab antibodies of the invention (including antigen-binding fragments thereof) and nucleic acids encoding antibodies of the invention (including antigen-binding fragments thereof). The antibodies of the invention can be used to treat, inhibit or prevent diseases, disorders or conditions associated with adalimumab. Anti-adalimumab antibodies of the invention can be provided in pharmaceutically acceptable compositions as known in the art or as described herein.

The anti-adalimumab antibodies of the invention may be administered alone or in combination with other types of treatments well known to those skilled in the art.

It is desirable to use high affinity and/or potent in vivo inhibiting and/or neutralizing antibodies of the present invention against adalimumab or fragments thereof, for both immunoassays directed to and therapy of disorders related to adalimumab. Such anti-adalimumab antibodies or antigen-binding fragments thereof will have a moderate to high affinity for adalimumab, including any fragments thereof. Suitable binding affinities include those with a dissociation constant or $K_D$ ranging from about $10^{-6}$ to about $10^{-12}$ M or even lower concentration. In one aspect, the $K_D$ ranges from about $10^{-8}$ to about $10^{-9}$ M.

Pharmaceutical compositions of the invention also can be administered in combination therapy, i.e., combined with other agents. For example, the combination therapy can include a composition of the present invention with at least one or more additional therapeutic agents, such as anti-inflammatory agents, DMARDs (disease-modifying anti-rheumatic drugs), immunosuppressive agents, as well as other pharmaceutical agents. The pharmaceutical compositions of the invention can also be administered in conjunction with other modes of therapy including, but not limited to, surgery, chemotherapy, radiation therapy and the like. Co-administration of a pharmaceutical composition of the present invention with other antibodies is also encompassed by the present invention.

As used herein, "pharmaceutically acceptable carrier" includes any and all solvents, dispersion media, coatings, antibacterial and antifungal agents, isotonic and absorption delaying agents, and the like that are physiologically compatible. In one aspect, the carrier is suitable for intravenous, intramuscular, subcutaneous, parenteral, spinal or epidermal administration (e.g., by injection or infusion). Depending on the route of administration, the active compound, i.e., antibody or antigen-binding portion thereof may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see, e.g., Berge, S. M., et al. (1977) J. Pharm. Sci. 66:1 19, the entire teaching of which is incorporated herein by reference). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978, the entire teaching of which is incorporated herein by reference.

To administer a compound of the invention by certain routes of administration, it may be necessary to coat the compound with, or co-administer the compound with, a material to prevent its inactivation. For example, the compound may be administered to a subject in an appropriate carrier, e.g., liposomes, or a diluent. Pharmaceutically acceptable diluents include saline and aqueous buffer solutions. Liposomes include water-in-oil-in-water CGF emulsions as well as conventional liposomes (Strejan et al. (1984) J. Neuroimmunol. 7:27, the entire teaching of which is incorporated herein by reference).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. In many cases, it will be desirable to include isotonic agents, e.g., sugars, polyalcohols such as mannitol, sorbitol, or sodium chloride in the composition. Prolonged absorption of the injectable compositions can be brought about by including in the composition an agent that delays absorption, e.g., monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, suitable methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response) and can be determined by a practitioner in the art. For example, a single bolus may be administered, several divided doses may be administered over time or the dose may be proportionally reduced or increased as indicated by the exigencies of the therapeutic situation. For example, the anti-adalimumab antibodies, including, but not limited to, antigen-binding portions thereof of the invention may be administered once or multiple times in a given time frame via subcutaneous injection. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylene-diamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about 90 percent of active ingredient, in one aspect from about 0.005 percent to about 70 percent, in yet another aspect from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, e.g., by the use of coating materials, such as lecithin, by the maintenance of the required particle size in the case of dispersions, and by the use of surfactants.

These compositions may also comprise adjuvants such as preservatives, wetting agents, emulsifying agents and dispersing agents. Prevention of presence of microorganisms may be ensured both by sterilization procedures well known in the art and by the inclusion of various antibacterial and antifingal agents, e.g., paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, e.g., 0.001 to 90% (in a particular aspect, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. A skilled practitioner will possess the knowledge necessary to evaluate and determine the proper dosage and mode of administration of the pharmaceutical compositions of the present invention. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. The administration may be intravenous, intramuscular, intraperitoneal, or subcutaneous. If desired, the effective daily dose of a therapeutic compositions may be administered as two, three, four, five, six or more sub-doses administered separately at appropriate intervals throughout the day, optionally, in unit dosage forms. It is possible for a compound of the present invention to be administered alone, however, it is possible to administer the compound as a pharmaceutical formulation (composition).

In one aspect, a problem related to adalimumab is determined. An adalimumab PK assay can be employed so as to determine how much adalimumab is circulating. With this information, one skilled in the art can arrive at an effective amount of anti-adalimumab to administer to a subject.

Experimentally this concept can be examined for its efficacy. Primates other than humans ("test subjects") can be administered adalimumab at different doses. Using a PK assay, the actual level of adalimumab can be ascertained and an L929 assay with serum from the test subject can determine the amount of active antibody. (The L929 assay is described in U.S. Pat. No. 6,090,382.) In different test subjects (who have been titered using adalimumab), different amounts of anti-adalimumab antibody can be administered to determine which amount is effective at neutralizing adalimumab.

Therapeutic compositions can be administered with medical devices known in the art. For example, a therapeutic composition of the invention can be administered with a needle-less hypodermic injection device, such as the devices disclosed in U.S. Pat. Nos. 5,399,163, 5,383,851, 5,312,335, 5,064,413, 4,941,880, 4,790,824, or 4,596,556, the entire teachings of which are herein incorporated by reference. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system, the entire teachings of which are incorporated herein by reference. Many other such implants, delivery systems, and modules are known to those skilled in the art.

In certain embodiments, the anti-adalimumab antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, e.g., in liposomes. For methods of manufacturing liposomes, see, e.g., U.S. Pat. Nos. 4,522,811; 5,374,548; and 5,399,331, the entire teachings of which are incorporated herein by reference. The liposomes may comprise one or more moieties which are selectively transported into specific cells or organs, thus enhance targeted drug delivery (see, e.g., V. V. Ranade (1989) J. Clin. Pharmacol. 29:685, the entire teaching of which is incorporated herein by reference). Exemplary targeting moieties include folate or biotin (see, e.g., U.S. Pat. No. 5,416,016 to Low et al., the entire teaching of which is incorporated herein by reference); mannosides (Umezawa et al., (1988) Biochem. Biophys. Res. Commun. 153:1038, the entire teaching of which is incorporated herein by reference); antibodies (P. G. Bloeman et al. (1995) FEBS Lett. 357:140; M. Owais et al. (1995) Antimicrob. Agents Chemother. 39:180, the entire teachings of which are incorporated herein by reference); surfactant protein A receptor (Briscoe et al. (1995) Am. J. Physiol. 1233:134, the entire teaching of which is incorporated herein by reference), different species of which may comprise the formulations of the inventions, as well as components of the invented molecules; p120 (Schreier et al. (1994) J. Biol. Chem. 269:9090, the entire teaching of which is incorporated herein by reference); see also K. Keinanen; M. L. Laukkanen (1994) FEBS Lett. 346:123; J. J. Killion; I. J. Fidler (1994) Immunomethods 4:273, the entire teachings of which are incorporated herein by reference. In one embodiment of the invention, the therapeutic compounds of the invention are formulated in liposomes; in another embodiment, the liposomes include a targeting moiety. In yet another embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

The composition must be sterile and fluid to the extent that the composition is deliverable by syringe. In addition to water, the carrier can be an isotonic buffered saline solution, ethanol, polyol (e.g., glycerol, propylene glycol, and liquid polyetheylene glycol, and the like), and suitable mixtures thereof. Proper fluidity can be maintained, e.g., by use of coating such as lecithin, by maintenance of required particle size in the case of dispersion and by use of surfactants. In many cases, it is desirable to include isotonic agents, e.g., sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, e.g., with an inert diluent or an assimilable edible carrier.

One embodiment of the present invention is directed to compositions and methods for the detection of adalimumab ("target") in a sample. The present method comprises contacting a sample with an anti-adalimumab antibody, or antigen binding portion thereof, under conditions suitable to from a complex between the anti-adalimumab antibody and adalimumab. Such suitable conditions are well known to those skilled in the art. The method further includes a detection system employed to detect this complex formation.

In one aspect of the present embodiment, the anti-adalimumab antibodies ("detection antibodies") are monoclonal antibodies produced from hybridomas suitable examples of which are 5A1-2A8 and 1H11-2E10 monoclonal antibodies described below.

The sample of the present embodiment can be any cell, tissue or fluid extract that can be prepared by any method well known to those skilled in the art. The source of the sample can be animal or plant. Both human and non-human can serve as a source for the sample. Illustrative examples of such sources that can provide a suitable sample include, but are not limited to, blood, urine, synovial fluid, organ tissue, tumor tissue masses, and the like.

In one aspect of the present embodiment, the detection antibodies are bound to an insoluble matrix such as that used in affinity chromatography or in an RIA or ELISA assay using methods well known to those skilled in the art. Other solid supports include, but are not limited to, glass, cellulose, polyacrylamide, nylon, polystyrene, polyvinyl chloride or polypropylene.

In another aspect, the detection antibodies can be unbound. Complex formation between one or more detection antibodies and its target from a sample can be accomplished in a batch analysis-type mechanism.

The anti-adalimumab antibody, or antigen binding portion thereof, can be attached to a detectable label using methods known in the art. Attachment can be accomplished by any chemical reaction that will bind the detectable marker and the anti-adalimumab antibody so long as the antibody and the marker retain their respective activities. The detection antibodies can be labeled using radioisotopes, alternatively, these antibodies can be labeled using detection markers such as a fluorescent moiety conjugated to the antibody, other methods well known to those skilled in the art such as enzyme-linkers and others are within the scope of this invention.

Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{3}H$, $^{14}$, $^{131}I$, $^{111}In$ or $^{99}Tc$. Labeling antibodies is well known to those skilled in the art. In one aspect, secondary antibodies, i.e., antibodies directed two the detection antibodies can be produced. There can be polyclonal secondary antibodies as well as monoclonal antibodies, the formation of each is well known to those skilled in the art. These secondary antibodies can be labeled and used to detect the detection antibodies.

The anti-adalimumab antibodies, or antigen binding portion thereof, of the invention can be used in a method for the detection of adalimumab and fragments and derivatives thereof in a subject by obtaining, e.g., a body fluid or tissue sample from the test subject and contacting the sample with one or more anti-adalimumab antibodies, or antigen binding portion thereof, of the invention under conditions suitable for the formation of antibody-antigen complexes. The presence or amount of such complexes can then be determined by methods described herein and otherwise known in the art (such as those described in O'Connor et al., (1988) Cancer Res 48:1361-66, and U.S. Pat. No. 7,232,891, the entire teachings of which are incorporated herein by reference), in which the presence or amount of complexes found in the test sample is compared to the presence or amount of complexes found in a series of standards or control samples containing a known amount of antigen. Accordingly, the present invention relates to methods for detecting adalimumab (or a fragment and/or derivative thereof) in a biological sample, blood, serum, urine, cerebrospinal fluid, mucus, or saliva.

One method for the detection of adalimumab and fragments thereof comprises contacting a sample with one or more anti-adalimumab antibodies, or antigen binding portions thereof, that specifically binds to adalimumab (or a fragment, modification and derivative thereof) under conditions suitable for the antibody to bind adalimumab, and then detecting the adalimumab-antibody complex. In this embodiment, if two or more antibodies are employed then it is possible for each antibody to recognize a different epitope of adalimumab. In one aspect, there is less than 10% cross reactivity between an anti-adalimumab antibodies, or antigen binding portions thereof, and a molecule other than adalimumab. In another aspect, there is less than 20% cross reactivity. In yet another aspect, there is less than 30% cross reactivity. In still another aspect, there is less than 40% cross reactivity. In yet another aspect, there is less than 50% cross reactivity.

In any of the described aspects for detecting adalimumab in a sample, the method can employ an immunoassay, e.g., an enzyme immunoassay (EIA), enzyme-linked immunosorbant assay (ELISA), radioimmunoassay (RIA), indirect competitive immunoassay, direct competitive immunoassay, non-competitive immunoassay, sandwich immunoassay, agglutination assay or other immunoassay describe herein and known in the art. (See, Zola, 1987, Monoclonal Antibodies: A Manual of Techniques, pp. 147 158, CRC Press, Inc., the entire teaching of which is incorporated herein by reference.)

Immunoassays for adalimumab and fragments/derivatives thereof may be constructed in heterogeneous or homogeneous formats. Heterogeneous immunoassays are distinguished by incorporating a solid phase separation of bound analyte from free analyte or bound label from free label. Solid phases can take a variety of forms well known in the art, including but not limited to tubes, plates, beads, and strips. One particular form is the microtiter plate. The solid phase material may be comprised of a variety of glasses, polymers, plastics, papers, or membranes. Particularly desirable are plastics such as polystyrene. Heterogeneous immunoassays may be competitive or non-competitive, i.e., sandwich, formats. (See, e.g., U.S. Pat. No. 7,195,882, the entire teaching of which is incorporated herein by reference.)

The present invention provides kits that can be used in the methods described above. In one embodiment, a kit comprises an anti-adalimumab antibody of the invention, or an antigen binding portion thereof as well as reagents necessary for facilitating an antibody-antigen complex, said reagents are well known to those skilled in the art. In one aspect, the kits of the present invention comprise a substantially isolated polypeptide comprising an epitope which is specifically immunoreactive with an anti-adalimumab antibody included in the kit. In one aspect, the kits of the present invention further comprise a control antibody which does not react with adalimumab or a fragment thereof. In another aspect, the kits of the present invention comprise a means used in the detection of binding of an anti-adalimumab antibody, or antigen binding portion thereof, to adalimumab or portion thereof (e.g., the detection antibody may be conjugated to a detectable substrate such as a fluorescent compound, an enzymatic substrate, a radioactive compound or a luminescent compound, or a second antibody which recognizes the first (detection) antibody and is, for example, conjugated to a detectable substrate).

EXAMPLE

Generation of Mouse Anti-Adalimumab Anti-Idiotypic Monoclonal Antibodies

Adalimumab was digested either with pepsin or papain and then purified using Protein A columns to produce F(ab)2 and Fab fragments, respectively. The purity and the biological activities of adalimumab fragments were verified by SDS-PAGE and L929 cytotoxicity bioassay, respectively. Balb/c mice were then serially immunized with adalimumab fragments. The sera collected after each immunization/booster were analyzed by ELISA. Mice with higher titers for adalimumab than for normal human IgG were selected for fusion using FO myeloma cells from ATCC. Spleens from selected mice were used to generate mouse hybridomas. Hybridoma supernatants were screened for antibodies binding specifically to adalimumab by differential ELISAs. Ninety-six well plates were coated either with 5 μg/mL of adalimumab or normal human IgG. Hybridoma supernatants were added and bound antibodies were detected by horse radish peroxidase coupled goat anti-mouse IgG antibody. Supernatants that had a positive reaction on adalimumab coated plates and a negative one on human IgG coated plates were further diluted at 1:10, 1:30 and 1:100 dilutions and re-tested for affinity ranking. Hybridomas whose secreted antibodies that had the strong binding to adalimumab were subcloned. Subclones were again screened by the ELISAs and several monoclonal antibodies were obtained.

Two monoclonal antibodies 5A1-2A8 and 1H11-2E10 were produced and analyzed. These monoclonal anti-adalimumab anti-idiotypic antibodies were produced from hybridoma cell lines that have been deposited with the American Type Culture Collection (ATCC), 10801 University Blvd, Manassas, Va. 20110-2209, under ATCC Designation Nos. PTA-8512 (1H11.2E10) and PTA-8513 (5A1-2A8) on Jun. 27, 2007. It should be understood that these monoclonal antibodies serve as an illustrative example and should not be interpreted as being limiting.

Anti-Idiotypic Anti-Adalimumab Mouse Monoclonal Antibody 5A1-2A8:

5A1-2A8 is a monoclonal mouse IgG1, kappa light chain antibody. Supernatant of 5A1-2A8 antibody producing hybridoma was tested on adalimumab and human IgG coated plates at several dilutions. At each dilution, 5A1-2A8 bound to adalimumab but not human IgG coated plates, Table 1. To test if human TNF would inhibit binding of 5A1-2A8 to adalimumab each dilution of supernatant was mixed with 100 µg/mL of human TNF before addition to adalimumab coated plates in ELISA. At each dilution, addition of TNF to the reaction mixture, did not significantly inhibited binding of 5A1-2A8 to adalimumab, Table 1. Thus, 5A1-2A8 could be described as a non-paratopic anti-idiotypic anti-adalimumab antibody. This antibody can bind adalimumab whether TNF is bound or not to the adalimumab antibody.

TABLE 1

Binding of 5A1-2A8 to adalimumab or human IgG, ELISA results

| Dilution of supernatant | Coating on the plate | Antigen addition | Optical Density |
| --- | --- | --- | --- |
| 1:10 | Human IgG | None | 0.1 |
| 1:10 | Adalimumab | None | 2.0 |
| 1:10 | Adalimumab | Human TNF | 1.9 |
| 1:30 | Human IgG | None | 0.1 |
| 1:30 | Adalimumab | None | 2.0 |
| 1:30 | Adalimumab | Human TNF | 1.8 |
| 1:100 | Human IgG | None | 0.1 |
| 1:100 | Adalimumab | None | 2.0 |
| 1:100 | Adalimumab | Human TNF | 1.6 |

5A1-2A8 was tested by itself in the TNF cytoxicity bioassay to test if it would mimic TNF. Addition of 5A1-2A8 to the culture medium was not toxic to the L929 cells, see, Carswell, E. A., et al. (1975) Proc. Natl. Acad. Sci. USA vol. 9, pp. 3666-3670, and U.S. Pat. No. 6,090,382 the entire teachings of which are incorporated herein by reference.

Affinity of 5A1-2A8 for adalimumab was tested in a BIAcore 2000 instrument. CM-3 biosensor chips were covalently coupled with goat anti-human IgG Fc polyclonal antibody. Adalimumab were injected at 0.2 mg/mL concentration, followed by varying concentrations of 5A1-2A8 ranging from 3.125 to 100 nM. Response units (RU) were recorded continuously for each concentration of 5A1-2A8 to create sensorgrams. Cell surface was regenerated by 10 mM glycine at pH1.5. The results are presented in Table 2.

TABLE 2

Binding of 5A1-2A8 to adalimumab, BIAcore results

| Analyte | RU | Ligand | [Ligand] | RU |
| --- | --- | --- | --- | --- |
| Adalimumab 0.2 mg/mL | 85 | Control | 0 nM | 0 |
| Adalimumab 0.2 mg/mL | 84 | 5A1-2A8 | 3.125 nM | 57 |
| Adalimumab 0.2 mg/mL | 77 | 5A1-2A8 | 6.25 nM | 72 |
| Adalimumab 0.2 mg/mL | 76 | 5A1-2A8 | 12.5 nM | 87 |
| Adalimumab 0.2 mg/mL | 80 | 5A1-2A8 | 20 nM | 98 |
| Adalimumab 0.2 mg/mL | 89 | 5A1-2A8 | 25 nM | 109 |
| Adalimumab 0.2 mg/mL | 82 | 5A1-2A8 | 40 nM | 107 |
| Adalimumab 0.2 mg/mL | 80 | 5A1-2A8 | 50 nM | 111 |
| Adalimumab 0.2 mg/mL | 80 | 5A1-2A8 | 80 nM | 114 |
| Adalimumab 0.2 mg/mL | 82 | 5A1-2A8 | 100 nM | 121 |

Binding sensorgrams were analyzed by bivalent analyte model supplied by the BIAcore and the kinetic parameters were derived, Table 3.

TABLE 3

Kinetic parameters of binding of 5A1-2A8 to adalimumab

| Antibody | On rate, M-1s-1 | Off rate, s-1 | Kd, M |
| --- | --- | --- | --- |
| 5A1-2A8 | $2.52 \times 10^5$ | $2.92 \times 10^{-4}$ | $1.16 \times 10^{-9}$ |

Anti-Idiotypic Anti-Adalimumab Mouse Monoclonal Antibody 1H11-2E10:

1H11-2E10 is a monoclonal mouse IgG1, kappa light chain antibody. Supernatant of 1H11-2E10 antibody producing hybridoma was tested on adalimumab and human IgG coated plates at several dilutions. At each dilution, 1H11-2E10 bound to adalimumab but not human IgG coated plates, Table 4. To test if human TNF would inhibit binding of 1H11-2E10 to adalimumab each dilution of supernatant was mixed with 100 µg/mL of human TNF before addition to adalimumab coated plates in ELISA. At each dilution, addition of TNF to the reaction mixture, inhibited binding of 1H11-2E10 to adalimumab, Table 4. Thus, 1H11-2E10 could be described as a paratopic anti-idiotypic anti-adalimumab antibody. This antibody can bind free adalimumab, but not TNF-bound adalimumab.

TABLE 4

Binding of 1H11-2E10 to adalimumab or human IgG

| Dilution of supernatant | Coating on the plate | Antigen addition | Optical Density |
| --- | --- | --- | --- |
| 1:10 | Human IgG | None | 0.1 |
| 1:10 | Adalimumab | None | 2.6 |
| 1:10 | Adalimumab | Human TNF | 0.5 |
| 1:30 | Human IgG | None | 0.1 |
| 1:30 | Adalimumab | None | 2.5 |
| 1:30 | Adalimumab | Human TNF | 0.2 |
| 1:100 | Human IgG | None | 0.1 |
| 1:100 | Adalimumab | None | 2.2 |
| 1:100 | Adalimumab | Human TNF | 0.1 |

1H11-2E10 was tested by itself in the TNF cytoxicity bioassay to test if it would mimic TNF. Addition of 1H11-2E10 to the culture medium was not toxic to the L929 cells.

Affinity of 1H11-2E10 for adalimumab was tested in a BIAcore 2000 instrument. CM-3 biosensor chips were covalently coupled with goat anti-human IgG Fc polyclonal antibody. Adalimumab were injected at 0.2 mg/mL concentration, followed by varying concentrations of 1H11-2E10 ranging from 3.125 to 100 nM. Response units (RU) were recorded continuously for each concentration of 1H11-2E10 to create sensorgrams. Cell surface was regenerated by 10 mM glycine at pH1.5. The results are presented in Table 5.

TABLE 5

Binding of 1H11-2E10 to adalimumab, BIAcore results

| Analyte | RU | Ligand | [Ligand] | RU |
|---|---|---|---|---|
| Adalimumab 0.2 mg/mL | 83.43 | Control | 0 nM | −0.26 |
| Adalimumab 0.2 mg/mL | 85.85 | 1H11-2E10 | 3.125 nM | 39.54 |
| Adalimumab 0.2 mg/mL | 86.35 | 1H11-2E10 | 6.25 nM | 59.75 |
| Adalimumab 0.2 mg/mL | 86.69 | 1H11-2E10 | 12.5 nM | 78.23 |
| Adalimumab 0.2 mg/mL | 85.34 | 1H11-2E10 | 20 nM | 88.24 |
| Adalimumab 0.2 mg/mL | 79.34 | 1H11-2E10 | 25 nM | 87.59 |
| Adalimumab 0.2 mg/mL | 78.72 | 1H11-2E10 | 40 nM | 96.62 |
| Adalimumab 0.2 mg/mL | 81.77 | 1H11-2E10 | 50 nM | 101.4 |
| Adalimumab 0.2 mg/mL | 91.46 | 1H11-2E10 | 80 nM | 122.21 |
| Adalimumab 0.2 mg/mL | 88.03 | 1H11-2E10 | 100 nM | 121.78 |

Binding sensorgrams were analyzed by bivalent analyte model supplied by the BIAcore and the kinetic parameters were derived, Table 6.

TABLE 6

Kinetic parameters of binding of 1H11-2E10 to adalimumab

| Antibody | On rate, M-1s-1 | Off rate, s-1 | Kd, M |
|---|---|---|---|
| 1H11-2E10 | $2.01 \times 10^5$ | $4.23 \times 10^{-3}$ | $2.10 \times 10^{-8}$ |

Measurement of Adalimumab Bound TNF Complexes:

Unbound TNF, like other cytokines, has a short half-life in vivo. When cytokines are bound by other proteins especially antibodies, these cytokines:antibody immune complexes have a longer half-life than unbound cytokines. Thus, in antibody treated subjects, the levels of cytokine:antibody complexes increase if there is constant production of the cytokine. It is of interest to identify patients with sustained production of TNF. Given that, e.g., monoclonal antibody 5A1-2A8 of the present invention is a non-paratopic anti-idiotypic anti-adalimumab antibody, it can be used in an ELISA format to detect TNF:adalimumab immune complexes. Also, 5A1-2A8 can be used to measure adalimumab independent of whether adalimumab is free of TNF or not (whereas, 1H11-2E10 can only be used to measure adalimumab when it is free of TNF). ELISA can be constructed such that the wells of a plate (e.g. a 96 well plate) can be coated using anti-human TNF antibody which binds to TNF at a different epitope other than adalimumab. After blocking the wells, samples comprising TNF:adalimumab complexes can be added and adalimumab can be detected by a labeled antibody against adalimumab, e.g., biotinylated 5A1-2A8 monoclonal antibody. Table 7 presents data of such an assay.

TABLE 7

Binding of labeled antibody to TNF: adalimumab complex

| Amount of TNF (ng/mL) in complex | Optical Density |
|---|---|
| 100 | 1.924 |
| 25.00 | 2.011 |
| 6.250 | 1.719 |
| 1.560 | 0.542 |
| 0.390 | 0.119 |
| 0.098 | 0.026 |

What is claimed is:

1. An isolated anti-adalimumab monoclonal antibody, or an antigen binding portion thereof, wherein said antibody is antibody 5A1-2A8, produced by a hybridoma having ATCC accession no. PTA-8513, or an antigen-binding portion thereof.

2. The antibody, or an antigen binding portion thereof, of claim 1 which is a Fab fragment or a single chain antibody.

3. A method of detecting adalimumab in a sample, said method comprising
    contacting said sample with the antibody, or antigen-binding portion thereof, of claim 1 under conditions suitable for antibody-antigen complex formation, and
    detecting a presence of the antibody-antigen complex formation, wherein detection of the complex indicates the presence of adalimumab in the sample.

4. The method of claim 3, wherein said detecting is selected from the group consisting of EIA (enzyme immunoassay), ELISA (enzyme linked immunosorbent assay), RIA (radioimmunoassay), indirect competitive immunoassay, direct competitive immunoassay, non-competitive immunoassay, sandwich immunoassay, and agglutination assay.

5. A kit comprising isolated anti-adalimumab monoclonal antibody 5A1-2A8, produced by a hybridoma having ATCC Accession No. PTA-8513, or an antigen-binding portion thereof.

6. The kit of claim 5 further comprising a control antibody, wherein said control antibody does not react with adalimumab or a fragment thereof.

7. A hybridoma cell line deposited under ATCC accession number PTA-8512.

8. An isolated anti-adalimumab monoclonal antibody, or an antigen binding portion thereof, wherein said antibody is 1H11-2E10, produced by a hybridoma having ATCC accession No. PTA-8512, or an antigen-binding portion thereof.

9. The antibody, or an antigen binding portion thereof, of claim 8 which is a Fab fragment or a single chain antibody.

10. A method of detecting adalimumab in a sample, said method comprising
    contacting said sample with the antibody, or antigen-binding portion thereof, of claim 8 under conditions suitable for antibody-antigen complex formation, and
    detecting a presence of the antibody-antigen complex formation, wherein detection of the complex indicates the presence of adalimumab in the sample.

11. The method of claim 10, wherein said detecting is selected from the group consisting of EIA (enzyme immunoassay), ELISA (enzyme linked immunosorbent assay), RIA (radioimmunoassay), indirect competitive immunoassay, direct competitive immunoassay, non-competitive immunoassay, sandwich immunoassay, and agglutination assay.

12. A kit comprising isolated anti-adalimumab monoclonal antibody 1H11-2E10, produced by a hybridoma having ATCC Accession No. PTA-8512, or an antigen-binding portion thereof.

13. The kit of claim 12 further comprising a control antibody, wherein said control antibody does not react with adalimumab or a fragment thereof.

14. A hybridoma cell line deposited under ATCC accession number PTA-8513.

* * * * *